US009004343B2

(12) United States Patent
Inoue et al.

(10) Patent No.: US 9,004,343 B2
(45) Date of Patent: Apr. 14, 2015

(54) SOLDERING APPARATUS

(75) Inventors: Hiroyuki Inoue, Saitama (JP); Tadayoshi Ohtashiro, Saitama (JP)

(73) Assignee: Senju Metal Industry Co., Ltd., Tokyo (JP)

( * ) Notice: Subject to any disclaimer, the term of this patent is extended or adjusted under 35 U.S.C. 154(b) by 147 days.

(21) Appl. No.: 13/083,413

(22) Filed: Apr. 8, 2011

(65) Prior Publication Data

US 2011/0247202 A1 Oct. 13, 2011

(30) Foreign Application Priority Data

Apr. 9, 2010 (JP) .................................. 2010-90968

(51) Int. Cl.

| | |
|---|---|
| *B23K 31/00* | (2006.01) |
| *B23K 31/02* | (2006.01) |
| *B23K 1/008* | (2006.01) |
| *G01N 29/30* | (2006.01) |
| *B23K 3/08* | (2006.01) |
| *B23K 1/00* | (2006.01) |
| *G01N 29/12* | (2006.01) |
| *G01R 33/07* | (2006.01) |
| *G01N 29/11* | (2006.01) |
| *B23K 1/002* | (2006.01) |

(Continued)

(52) U.S. Cl.
CPC ............ *B23K 1/008* (2013.01); *Y10T 29/53022* (2015.01); *G01N 29/30* (2013.01); *B23K 3/08* (2013.01); *B23K 1/0008* (2013.01); *G01N 29/12* (2013.01); *G01R 33/07* (2013.01); *G01N 29/11* (2013.01); *B23K 1/002* (2013.01); *B23K 3/0475* (2013.01); *B23K 1/0016* (2013.01); *B23K 1/012* (2013.01); *B23K 3/047* (2013.01); *B23K 2201/42* (2013.01); *H05K 3/3494* (2013.01)

(58) Field of Classification Search
CPC .... B23K 1/0008; B23K 1/002; B23K 3/0475; B23K 3/08; G01N 2291/044; G01N 2291/2672; G01N 29/11; G01N 29/12; G01N 29/30; G01R 33/07
USPC ....................... 228/178–180.22, 245–255, 37
See application file for complete search history.

(56) References Cited

FOREIGN PATENT DOCUMENTS

| | | |
|---|---|---|
| JP | 07-212027 | 8/1995 |
| JP | 2000000553 A | 1/2000 |

(Continued)

OTHER PUBLICATIONS

JP 2002115885 A computer translation.*

(Continued)

*Primary Examiner* — Erin Saad
(74) *Attorney, Agent, or Firm* — Chernoff, Vilhauer, McClung & Stenzel, LLP

(57) ABSTRACT

In a reflow soldering apparatus, air heated by heaters is blown by fans onto a printed circuit board. Temperature controllers that control temperature of the heaters supply operation amount thereof to a calculation unit that calculates consumed electric energy of soldering apparatus. Inverters that control revolution of fans supply a value of current to the calculation unit. A control unit supplies a coefficient of the consumed electric energy to the calculation unit. The calculation unit calculates a total amount of consumed electric energy of the reflow soldering apparatus based on the operation amount, value of current and coefficient of the consumed electric energy thus obtained. A display unit displays on an operation screen the total amount of consumed electric energy of the reflow soldering apparatus, which has been calculated by the calculation unit.

10 Claims, 10 Drawing Sheets

(51) Int. Cl.
    *B23K 3/047*     (2006.01)
    *B23K 1/012*     (2006.01)
    *H05K 3/34*     (2006.01)

(56) References Cited

FOREIGN PATENT DOCUMENTS

| JP | 2002115885 A | * | 4/2002 |
| JP | 2005352614 A | | 12/2005 |
| JP | 2008134727 A | * | 6/2008 |
| JP | 2010015207 A | | 1/2010 |

OTHER PUBLICATIONS

JP07-212027A computer translation.*
Computer english translation of JP 2008134727 A.*
Thierry Jeggy, European Search Report for EP 11161785, Jul. 5, 2011.

* cited by examiner

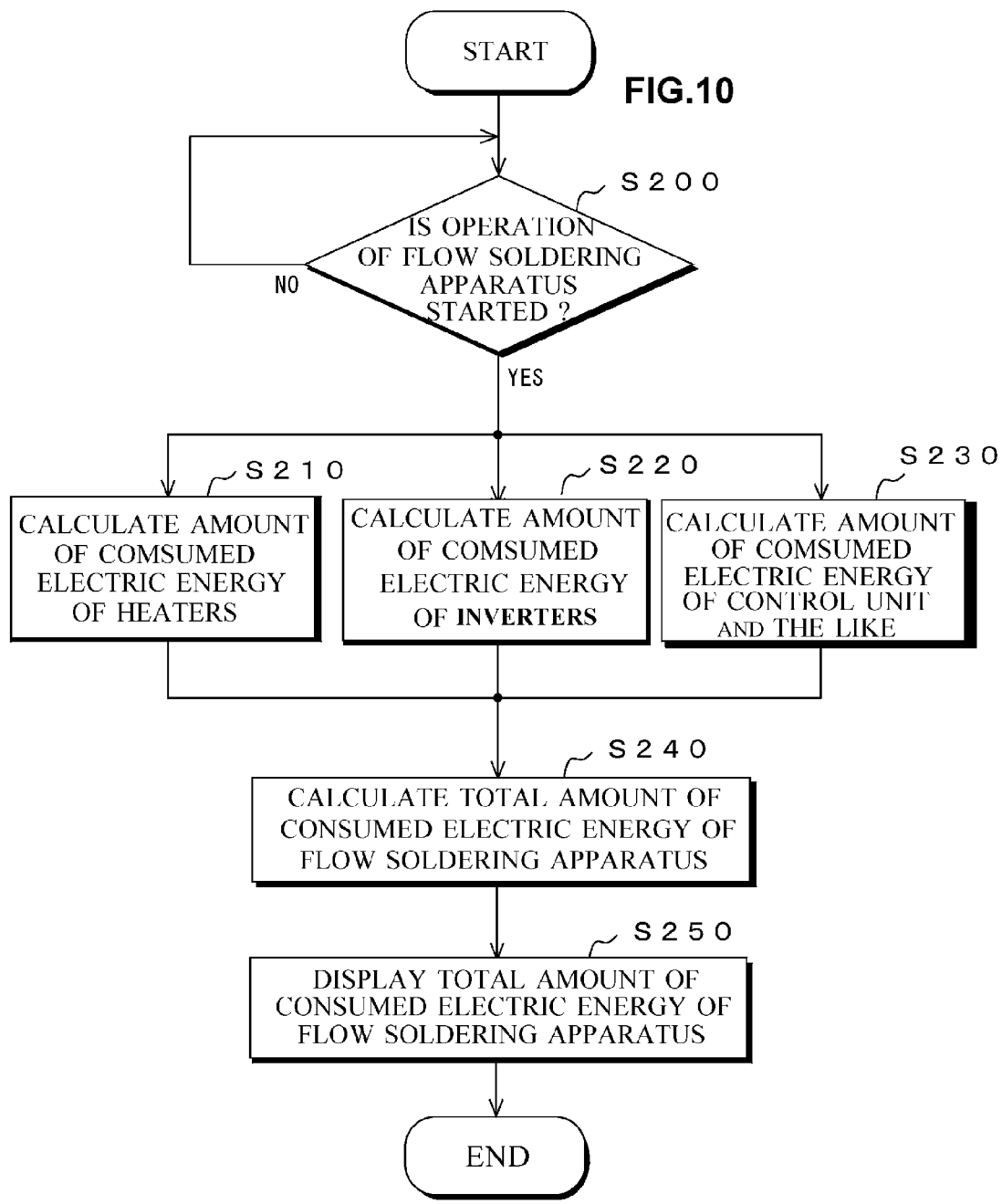

SOLDERING APPARATUS

CROSS REFERENCES TO RELATED APPLICATIONS

The present invention contains subject matter related to Japanese Patent Application JP 2010-090968 filed in the Japanese Patent Office on Apr. 9, 2010, the entire contents of which being incorporated herein by reference.

BACKGROUND OF THE INVENTION

1. Field of the Invention

The present invention relates to a soldering apparatus that solders electronic components on a circuit board using solder composition.

2. Description of Related Art

When soldering the electronic components on a printed circuit board, a reflow soldering apparatus is generally used. Such a reflow soldering apparatus includes a conveyor conveying the printed circuit boards and a main body of the reflow soldering apparatus into which the conveyor conveys the print circuited boards.

The main body of the reflow soldering apparatus is partitioned into three zones, namely, a preliminary heating zone, a main heating zone and a cooling zone therein. For example, each of the preliminary heating and main heating zones contains heaters, temperature controllers, motors and inverters. The cooling zone contains cooling fans and inverters. Any electronic components are mounted on the printed circuit board on which solder paste has been previously printed. The printed circuit board is then subjected to the heating in the soldering apparatus, so that the electronic components can be soldered on the printed circuit board.

Here, the general reflow soldering apparatus is equipped with electricity meters that measures an amount of consumed electrical energy in the operation of the reflow soldering apparatus. Each of the temperature controllers that control temperatures of the above-mentioned heaters or each of the inverters that control rotations of the motors driving the fans is equipped with such an electricity meter. The electricity meter displays the amount of consumed electrical energy of each of the heaters or fans.

Such a measurement is also performed in a flow type soldering apparatus in which solder melted within a solder bath is flown and electronic components are soldered on the printed circuit board by contacting a lower surface of the printed circuit board to atop layer of flown solder. This flow soldering apparatus (including partial soldering apparatus of the printed circuit board) is provided with a fluxer, preheaters, a flow solder bath, cooling device and the like. The preheaters are connected with the temperature controller that controls temperature thereof. The flow solder bath is connected with an inverter that controls a number of revolutions of each of the motors which drive screws. The temperature controller and the inverter are respectively equipped with the above-mentioned electricity meters which indicate the amount of consumed electrical energy of each of the heaters or motors.

Japanese Patent Application Publication No. H07-212027 has disclosed a heaters-starting-up method in which in a reflow soldering apparatus, heaters provided in the furnace start up with starting-up time of each heater being staggered so that a total amount of current of the heaters at the starting-up time thereof may be reduced.

SUMMARY OF THE INVENTION

In a method of obtaining the amount of consumed electrical energy of the past reflow soldering apparatus or the past flow soldering apparatus, however, the temperature controller, the inverter and the like may be respectively required so to be equipped with the above-mentioned electricity meters. This may cause an increase in costs in accordance with numbers of equipped electricity meters. Further, each device is equipped with electricity meter, which increases spaces for equipping the electricity meters excessively.

In Japanese Patent Application Publication No. H07-212027, only a total amount of currents in the heaters is taken into consideration, but consumed electrical energy or the like of other parts such as motors that drive fans is not taken into consideration. A total amount of actually consumed electrical energy of the soldering apparatus is not taken into consideration.

Thus, the present invention solves the above-mentioned problems and it has an object to provide a soldering apparatus that allows any costs to be reduced and/or allows any spaces to be reduced in a case of obtaining the consumed electrical energy of the soldering apparatus.

According to an embodiment of the present invention, there is provided a soldering apparatus that solders an electronic component on a circuit board using a solder composition. The soldering apparatus contains a soldering unit that solders the electronic component on the circuit board and a detection unit that detects information of consumed electric energy, the information relating to an amount of the consumed electric energy of the soldering unit. The soldering apparatus also contains a calculation unit that obtains the information of consumed electric energy of the soldering unit which is detected by the detection unit and calculates the amount of the consumed electric energy of the soldering unit based on the obtained information of consumed electric energy of the soldering unit, and a display unit that displays on a screen thereof the amount of the consumed electric energy of the soldering unit, which is calculated by the calculation unit.

In the embodiments of the soldering apparatus relating to the present invention, the soldering apparatus contains a reflow soldering apparatus that solders an electronic component(s) on a circuit board to which the solder composition is previously applied, and a flow soldering apparatus that solders an electronic component (s), which is previously mounted on a circuit board, on the circuit board by flowing solder melted in a solder bath.

The soldering unit such as heaters and fans solders the electronic component(s) on the circuit board conveyed into the soldering apparatus under heating processing, cooling processing and/or the like. Then, the detection unit detects information of consumed electric energy. This information relates to an amount of the consumed electric energy of the soldering unit during soldering processing. The detection unit includes a temperature controller that controls temperature of heaters and an inverter that controls a number of revolutions of each motor. The information of consumed electric energy of the soldering unit includes an amount of operation of the temperature controller, a value of current from the inverter and a predetermined coefficient of the consumed electric energy. The calculation unit obtains the information of consumed electric energy of the soldering unit which is detected by the detection unit and calculates the amount of the consumed electric energy of the soldering unit based on the obtained information of consumed electric energy of the soldering unit. The display unit displays on a screen thereof the amount of the consumed electric energy of the soldering unit, which is calculated by the calculation unit. The detection unit also detects information on consumed electric energy of the detection unit itself. The calculation unit obtains the information of consumed electric energy of the soldering unit and the information of consumed electric energy of the detection unit and calculates a total amount of the consumed electric energy of the soldering apparatus based on the obtained information of the consumed electric energy of the soldering unit and the obtained information of the consumed electric energy of the detection unit. The display unit displays the total amount of the consumed electric energy of the soldering apparatus, which is calculated by the calculation unit.

Thus, according to the embodiments of the invention, the calculation unit calculates amounts of the consumed electric energy of the soldering unit and the detection unit and the total amount of the total amount of the consumed electric energy of the soldering apparatus. The display unit displays the amounts of the consumed electric energy of the soldering unit and the detection unit and the total amount of the total amount of the consumed electric energy of the soldering apparatus, which have been calculated by the calculation unit. This enables electricity meters installed in each soldering unit like those in the past soldering apparatus to be unnecessary so that it is possible to reduce any spaces in the soldering apparatus. Further, an electricity meter installed in each of the parts of the reflow soldering apparatus may be unnecessary so that it is possible to reduce any costs in the soldering apparatus.

The concluding portion of this specification particularly points out and directly claims the subject matter of the present invention. However, those skilled in the art will best understand both the organization and method of operation of the invention, together with further advantages and objects thereof, by reading the remaining portions of the specification in view of the accompanying drawing(s) wherein like reference characters refer to like elements.

BRIEF DESCRIPTION OF THE DRAWINGS

FIG. 10 is a flowchart showing an operation example of the flow soldering apparatus.

DESCRIPTION OF THE PREFERRED EMBODIMENTS

Figure 1:
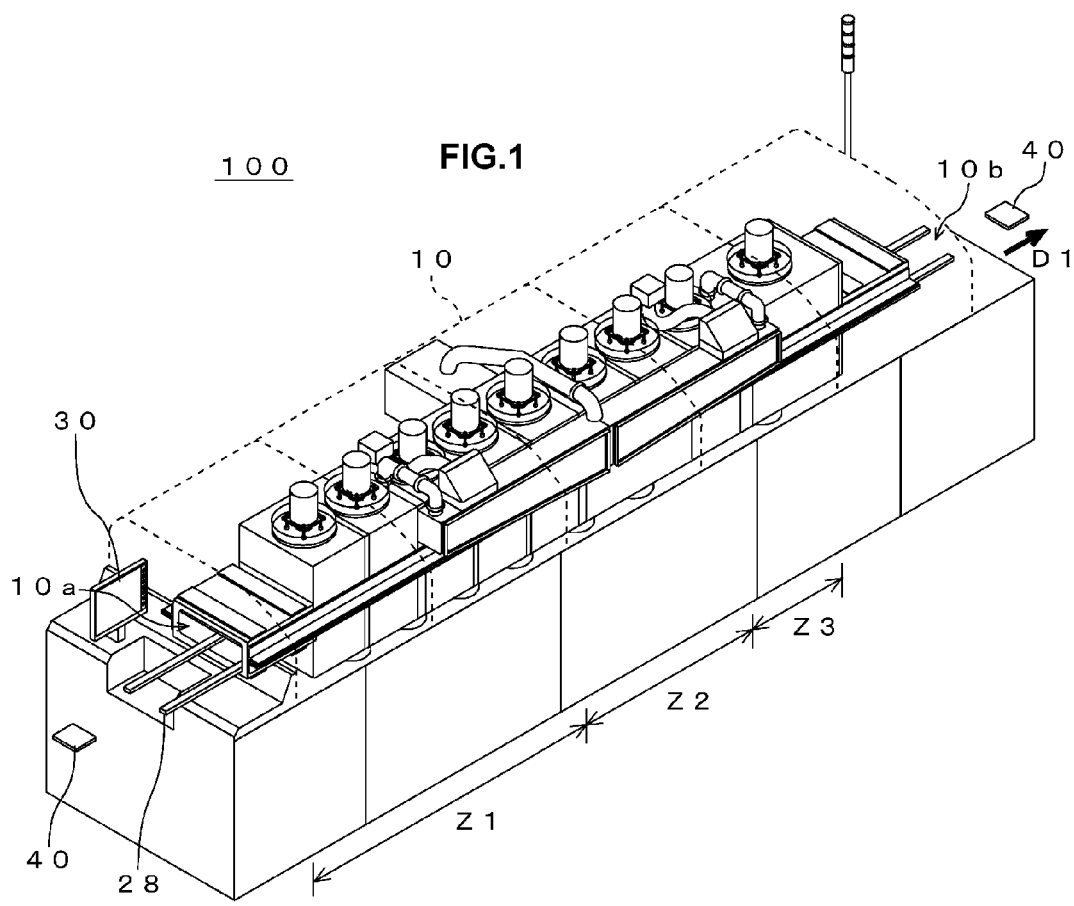
FIG. 1 is a diagram showing a configuration example of a reflow soldering apparatus as a first embodiment of the invention.

The following will describe embodiments of the invention with reference to drawings.

1. First Embodiment

Configuration Example of Reflow Soldering Apparatus

A reflow soldering apparatus 100 as a first embodiment of the invention obtains an amount of operation Dtr indicating consumed electric energy of heaters 12 from temperature controllers 20, an amount of current Dir indicating consumed electric energy of the motors 16, each of which drives fan 14, from inverters 22 and the like. The reflow soldering apparatus 100 calculates an amount of the consumed electric energy of heaters 12 and an amount of the consumed electric energy of the motors 16 and adds up amounts of the consumed electric energy thus calculated to display a total amount of consumed energy of the soldering apparatus on a screen of an operation/display unit 30.

The reflow soldering apparatus 100 contains a main body (muffle furnace) 10 of the reflow soldering apparatus, a conveyor 28, and the operation/display unit 30, as shown in FIG. 1. The main body 10 of the reflow soldering apparatus 100 is formed of a tunnel-like housing including the entrance 10a and the exit 10b. The inside of the main body 10 of the reflow soldering apparatus 100 is partitioned into three zones, namely, a preliminary heating zone Z1, a main heating zone Z2 and a cooling zone Z3, along the conveying route of the circuit board from the entrance 10a up to the exit 10b. The conveyor 28 extends along the conveying route from the entrance 10a up to the exit 10b and conveys each of the printed circuit boards 40 at a predetermined speed from the entrance 10a of the main body 10 of the reflow soldering apparatus 100 to the exit 10b thereof (along a direction of an arrow X).

When the printed circuit board 40 on which surface-mountable electronic components are mounted is set on the conveyor 28, the printed circuit board 40 is conveyed to enter into the main body 10 of the reflow soldering apparatus 100 through the entrance 10a. In the preliminary heating zone Z1 of the main body 10 of the reflow soldering apparatus 100, heated air is blown upon the printed circuit board 40. This enables flux to be activated. This also enables to be deleted an oxidation layer on a surface of electrode or solder paste. Next, when conveying the printed circuit board 40 into the main heating zone Z2, the solder is melted so that electronic components can be fixed on electrodes of the printed circuit board 40. Finally, when conveying the printed circuit board 40 into the cooling zone Z3, the printed circuit board 40 is cooled so that the solder can be solidified. The printed circuit board 40 cooled through the cooling zone Z3 is discharged from the exit 10b.

Figure 2:
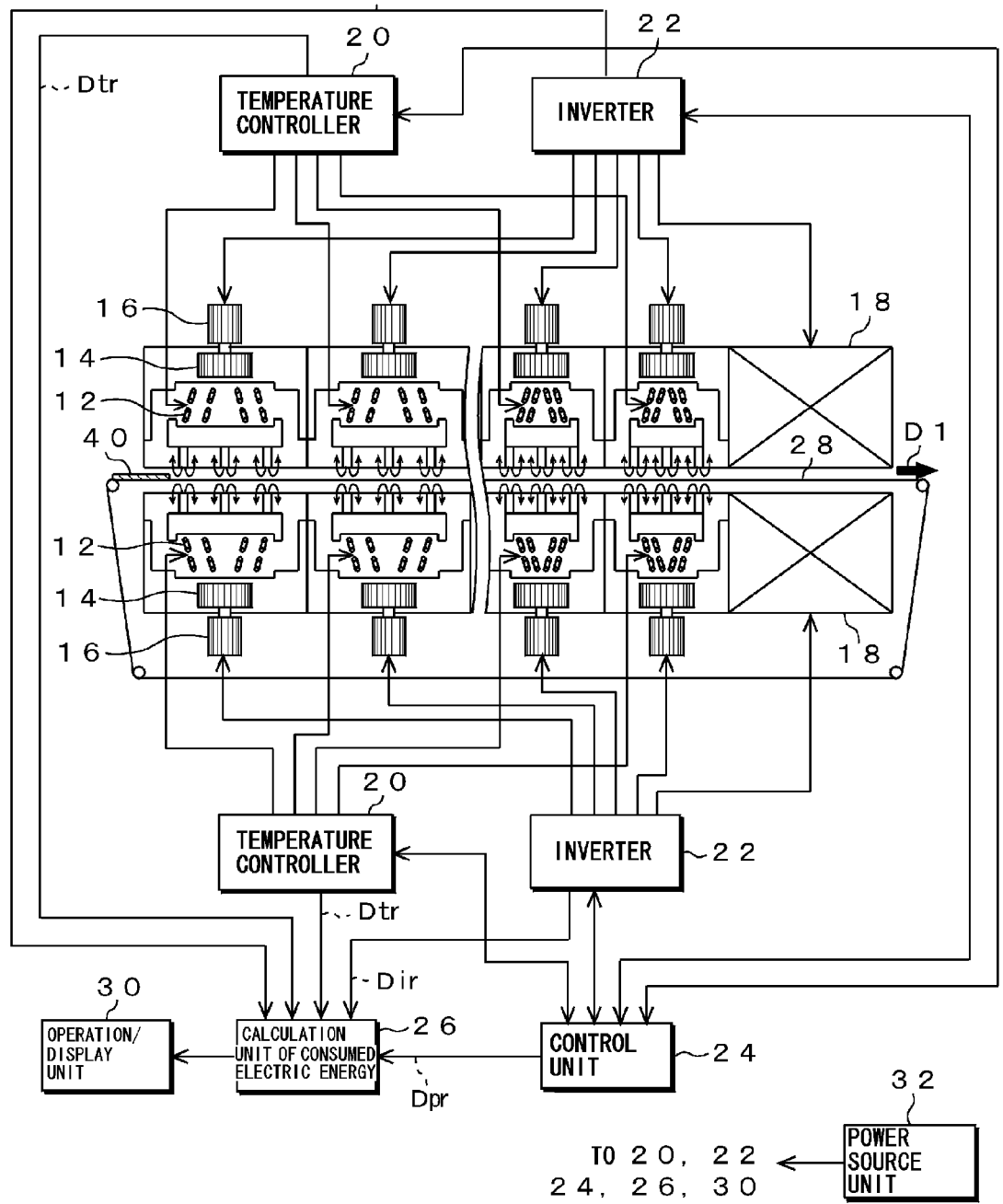
FIG. 2 is a block diagram showing a configuration of the reflow soldering apparatus.

The following will describe an internal configuration of the above-mentioned reflow soldering apparatus 100 with reference to the block diagram of FIG. 2. As shown in FIG. 2, the reflow soldering apparatus 100 contains a power source unit 32, a control unit 24, heaters 12, temperature controllers 20, motors 16, fans 14, inverters 22, cooling devices 18, a calculation unit 26 of consumed electric energy and an operation/display unit 30. It is to be noted that the heaters 12, the motors 16 and the fans 14 constitute a soldering unit as an example thereof. The temperature controllers 20, the inverters 22 and the control unit 24 constitute a detection unit as an example thereof.

The power source unit 32 is connected to the control unit 24, the heaters 12, the temperature controllers 20, the motors 16, the fans 14, the inverters 22, the cooling devices 18, the calculation unit 26 of consumed electric energy and the operation/display unit 30, respectively and supplies power source to each of the parts.

The control unit 24 is composed of a personal computer or the like, which includes a central processing unit (CPU), a read only memory (ROM), a random access memory (RAM). This control unit 24 is connected to the temperature controllers 20, the inverters 22 and the calculation unit 26 of consumed electric energy and controls operations of the temperature controllers 20, the inverters 22 and the calculation unit 26 of consumed electric energy. Since consumed electric energy of the control unit 24 is changed within a fixed range thereof, a fixed amount of the consumed electric energy is previously set as a coefficient Dpr of consumed electric energy. The control unit 24 reads the coefficient Dpr of consumed electric energy recorded in a memory to output it to the calculation unit 26 of consumed electric energy.

Pairs of the heaters 12 are disposed on upper and lower positions of the conveyor 28 so that the heaters are opposed and heat air within the main body 10 of the reflow soldering apparatus 100 under power control of the temperature controllers 20 (for example, PID control). In this embodiment, as shown in FIG. 1, four pairs of the heaters 12 are disposed on upper and lower positions of the conveyor 28 in the preliminary heating zone Z1 and four pairs of the heaters 12 are disposed on upper and lower positions of the conveyor 28 in the main heating zone Z2. It is to be noted that the preliminary heating zone Z1 and the main heating zone Z2 may often have the same configuration generally but they may have different configurations, a description of which will be omitted as a matter of convenience.

The temperature controllers 20 that control temperature of the heaters 12 have temperature sensors and temperature adjustment units. In this embodiment, the temperature controllers 20 are constituted of a pair of upper and lower temperature controllers. The temperature controllers 20 may be provided in each of the heating zones Z1 and Z2. Each of the temperature sensors is composed of a thermocouple or a thermistor and is set near the heater 12 to be controlled to measure temperature of the heater 12 or around the heater 12. The temperature adjustment units perform proportional, integral and derivative (PID) control based on temperature information detected by the temperature sensors. In the PID control, the amount of operation Dtr is adjusted so that it becomes a set temperature (target temperature). The amount of operation Dtr includes output voltage, output current or the like of each of the heaters 12, on which the temperature of each of the heaters 12 is set to the set temperature. Further, the temperature controllers 20 detect the amount of operation Dtr of the heaters 12 as an amount of temperature control thereof and output it to the calculation unit 26 of consumed electric energy.

Pairs of the motors 16 are disposed on upper and lower positions of the conveyor 28 so that the motors are opposed and respectively drive under a frequency control by the inverters 22 to rotate the fans 14 at a predetermined number of revolutions. Each of the fans 14 is composed of, for example, a air-supplying fan such as a turbofan or a sirocco-fan and rotates by the rotation of each of the motors 16 to blow air heated by each of the heaters 12 to each of the upper and lower surfaces of the printed circuit board 40. In this embodiment, four pairs of the motors 16 and four pairs of the fans 16 are disposed on upper and lower positions of the conveyor 28 in the preliminary heating zone Z1 and four pairs of the motors 16 and four pairs of the fans 16 are disposed on upper and lower positions of the conveyor 28 in the main heating zone Z2. It is to be noted that the fans 14 and the motors 16 may have the different configurations in the preliminary heating zone Z1 and the main heating zone Z2 and they may have the same configuration but have different use conditions such as different power to be supplied, a description of which will be omitted as a matter of convenience.

Each of the cooling devices 18 contains a motor, not shown, and a cooling fan, not shown, and drives the motor under a frequency control by the inverters 22 to rotate the cooling fan at a predetermined number of revolutions. This enables cooled air to be blown to the printed circuit board 40 so that the printed circuit board heated in the preliminary heating zone Z1 and the main heating zone Z2 can be cooled.

The inverters 22 convert a frequency of power source (alter an amount of current Dir) based on any control information supplied from the control unit 24 to control the number of revolutions of each of the motors 16. In this embodiment, a pair of the inverters, each of which controls the upper motors or the lower motors, is used. It is to be noted that the inverter 22 may be provided on each of the motors 16. The inverters 22 detect and obtain the amount of current Dir output when they drive the motors 16 to output the amount of current Dir to the calculation unit 26 of consumed electric energy.

The calculation unit 26 of consumed electric energy is connected to the temperature controllers 20, the inverters 22 and the control unit 24, respectively, and is composed of, for example, a computer having CPU, ROM RAM and the like. The calculation unit 26 of consumed electric energy obtains the amount of operation Dtr from the temperature controllers 20 and calculates consumed electric energy of the heaters 12 from output voltage, output current and the like included in the amount of operation Dtr thus obtained. The calculation unit 26 of consumed electric energy also obtains the amount of current Dir used for driving the motors 16 from the inverters 22 and calculates consumed electric energy of the motors 16 from the amount of current Dir thus obtained. The calculation unit 26 of consumed electric energy further obtains the coefficient Dpr of consumed electric energy read from the control unit 24 and calculates consumed electric energy of the control unit 24 from the coefficient Dpr of consumed electric energy thus obtained. Such consumed electric energy of the control unit 24 thus calculated includes consumed electric energy of parts other than the control unit 24 such as the temperature controllers 20 and/or the inverters 22. Next, the calculation unit 26 of consumed electric energy adds up the calculated amount of consumed electric energy of the temperature controllers 20, the calculated amount of consumed electric energy of the inverter 22 and the calculated amount of consumed electric energy of the control unit 24 and the like to calculate a total amount of consumed electric energy of the reflow soldering apparatus 100. The calculation unit 26 of consumed electric energy then outputs the calculated total amount of consumed electric energy of the reflow soldering apparatus 100 to the operation/display unit 30 which displays the total amount of consumed electric energy of the reflow soldering apparatus 100 on a window of representing the consumed electric energy of the reflow soldering apparatus 100 in an operation screen of the operation/display unit 30.

The operation/display unit 30 is composed of, for example, a touch panel operation device and a display device such as liquid crystal display or an organic electroluminescent display so that they are incorporated. The operation/display unit 30 displays the total amount of consumed electric energy of the reflow soldering apparatus 100 based on the information on consumed electric energy supplied from the calculation unit 26 of consumed electric energy on the operation screen of the operation/display unit 30 (see FIG. 3). The operation/display unit 30 also inputs setting of the temperature of each of the heating zones Z1 and Z2 and setting of an amount level of blown air and/or a conveying speed of the conveyor 28 by pressing pairs of up-down control arrow buttons and supplies the input operation information to the control unit 24.

[Representation Example in Operation Screen of Operation/Display Unit]

Figure 3:
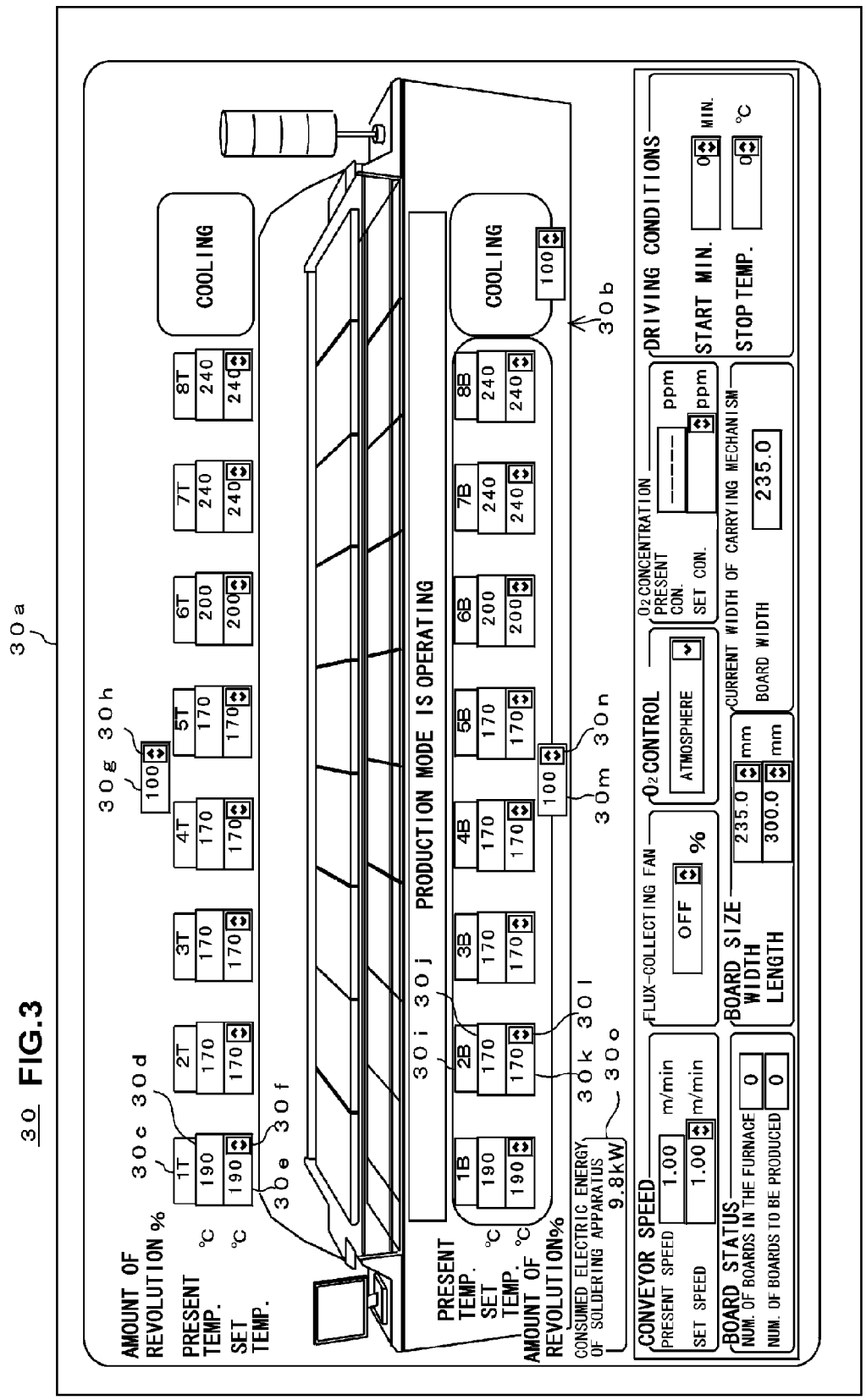
FIG. 3 is a diagram (No. 1) showing a representation example of a screen of an operation/display unit in the reflow soldering apparatus.

The following will describe a representation example of the operation screen 30a to be displayed on the operation/display unit 30. As shown in FIG. 3, an image 30b of the reflow soldering apparatus 100, which indicates the reflow soldering apparatus 100 schematically, appears at a middle of the operation screen 30a of the operation/display unit 30. In the image 30b of the reflow soldering apparatus, the reflow soldering apparatus having two upper and lower groups of the preliminary heating zone Z1 and the main heating zone Z2 is shown.

In the upper group of the preliminary heating zone Z1 and the main heating zone Z2, letters 30c such as 1T through 8T indicating respective zones are shown at a top of each zone. Present temperature 30d indicating actual temperature of each zone is shown below the letters 30c of each of the zones 1T through 8T. Set temperature 30e of each of the zones 1T through 8T which a user sets is shown below the present temperature 30d. A pair of up-down arrow keys 30f is shown at right side of the set temperature 30e and by operating the up-down control arrow keys 30f, the set temperature 30e of each of the zones 1T through 8T can be adjusted for every one degree.

Letters 30g indicating a level of an amount of revolution by the fan 14 are shown above and between the zones 4T and 5T. A pair of up-down control arrow keys 30h for adjusting the level of the amount of revolution by the fan 14 is shown at right side of the letters 30g.

In the lower group of the preliminary heating zone Z1 and the main heating zone Z2, letters 30i such as 1B through 8B indicating respective zones are shown at a top of each zone in a casing shown in the image 30b of the reflow soldering apparatus. Present temperature 30j indicating actual temperature of each of the zones 1B through 8B is shown below the letters 30i of each of the zones 1B through 8B. Set temperature 30k of each of the zones 1B through 8B which a user sets is shown below the present temperature 30j. A pair of up-down arrow keys 30l is shown at right side of the set temperature 30k and by operating the up-down arrow keys 30l, the set temperature 30k of each of the zones 1B through 8B can be adjusted for every one degree.

Letters 30m indicating a level of an amount of revolution by the fan 14 are shown below and between the zones 4B and 5B. A pair of up-down arrow keys 30n for adjusting the level of the amount of revolution by the fan 14 is shown at right side of the letters 30m.

A representation window 30o for representing figure(s) indicating the total amount of consumed electric energy of reflow soldering apparatus 100 is shown at left side of the screen and below the image 30b of the reflow soldering apparatus 100. In the representation window 30o, the total amount of the consumed electric energy of reflow soldering apparatus 100, which have been calculated in the above-mentioned calculation unit 26 of consumed electric energy, is represented. The total amount of the consumed electric energy of reflow soldering apparatus 100 is updated and displayed on a real-time basis or at regular interval. It is to be noted that when the user selects the representation window 30o, a pop-up sub-screen for representing consumed electric energy of the heaters 12 or the motors 16 may be shown. Further, when the total amount of the consumed electric energy of reflow soldering apparatus 100 exceeds a predetermined value, the representation window 30o may be flushed or highlighted based on a determination of the calculation unit 26 of consumed electric energy and/or the control unit 24.

Below the representation window 30o of the operation screen 30b of the operation/display unit 30, various kinds of information on a speed of conveyor, flux-collecting fan, oxygen ($O_2$) control, oxygen ($O_2$) concentration, board status, board size, current width of carrying mechanism and driving conditions, are shown.

Figure 4:
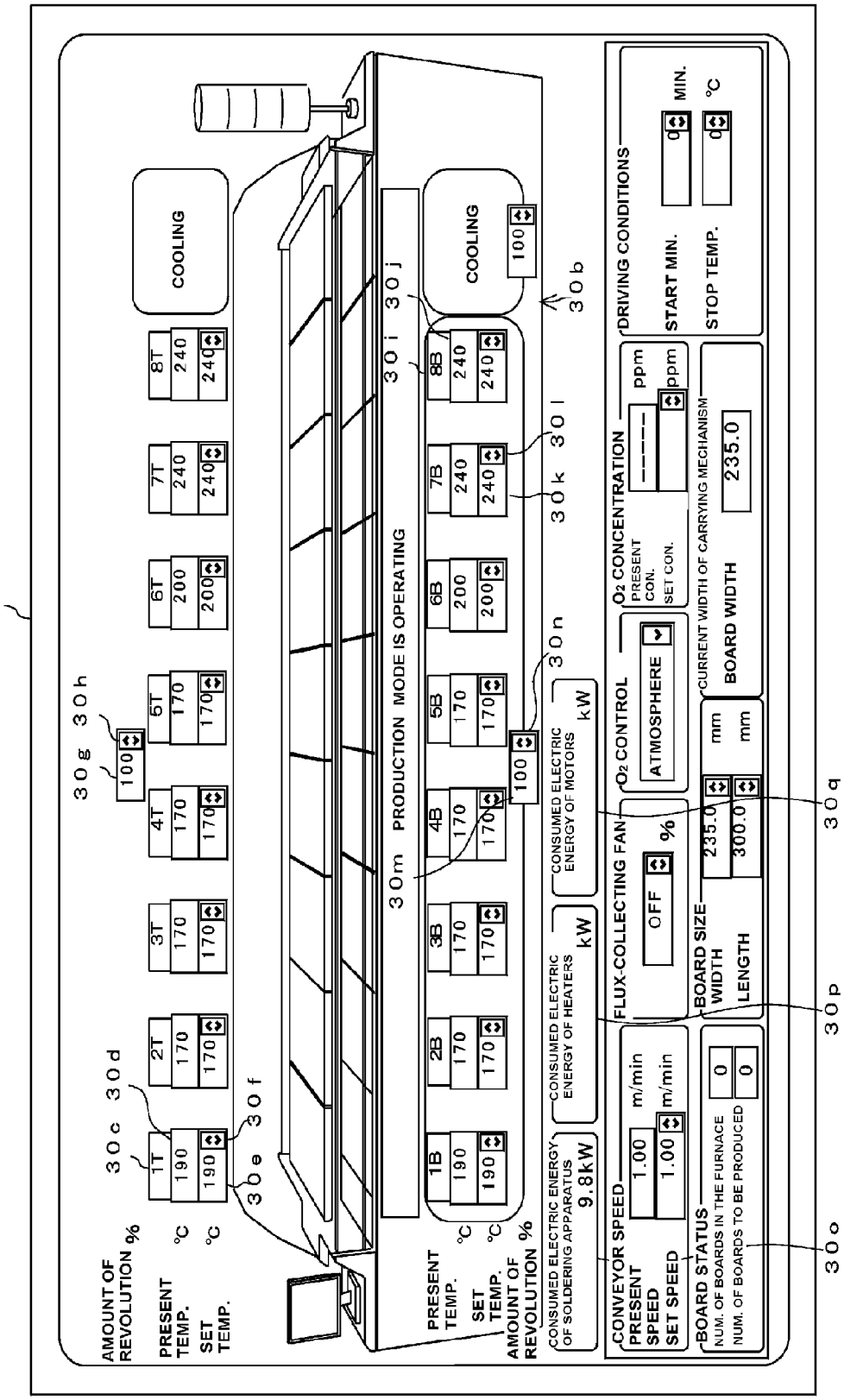
FIG. 4 is a diagram (No. 2) showing the representation example of the screen of the operation/display unit in the reflow soldering apparatus.

A representation window for representing consumed electric energy of respective parts such as the heaters 12 or the motors 16 other than the representation window 30o indicating the total amount of consumed electric energy of reflow soldering apparatus 100 may be shown. For example, as shown in FIG. 4, a representation window 30p for representing consumed electric energy of the heaters 12 may be represented at a right side of the representation window 30o and a representation window 30q for representing consumed electric energy of the motors 16 may be represented at a right side of the representation window 30p. This enables the consumed electric energy of the parts of the reflow soldering apparatus 100 to be known in detail so that the consumed electric energy of the reflow soldering apparatus 100 can be controlled in detail. As a result thereof, efficient energy saving of whole of the reflow soldering apparatus 100 can be accomplished.

[Operation Example of Reflow Soldering Apparatus]

Figure 5:
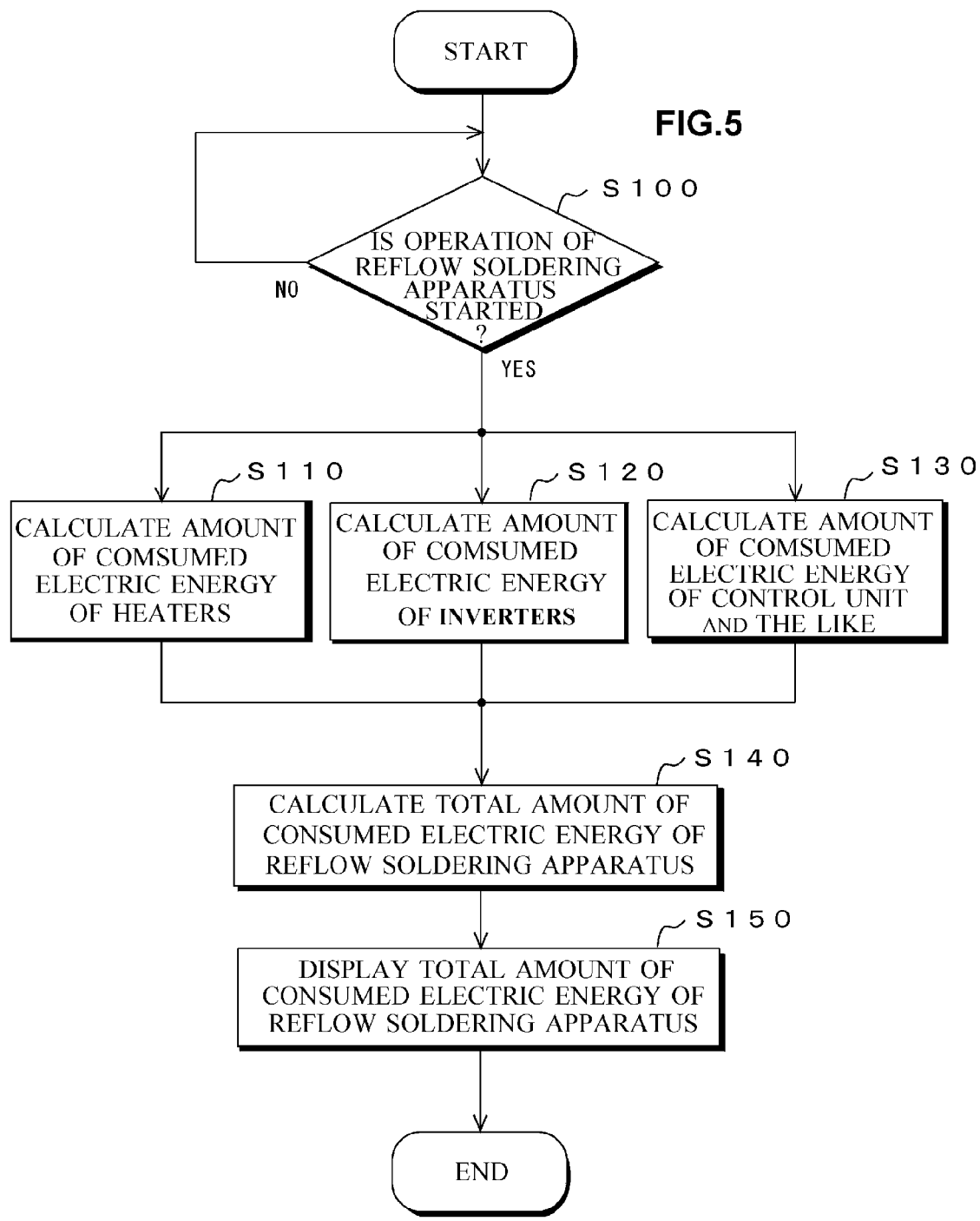
FIG. 5 is a flowchart showing an operation example of the reflow soldering apparatus.

The following will describe an operation example of the reflow soldering apparatus 100 according to the invention. As shown in FIG. 5, at step S100, the calculation unit 26 of consumed electric energy determines whether or not the operation of the reflow soldering apparatus 100 is started. For example, it determines whether or not the user selects an operation button for powering the power source on in the operation/display unit 30. If the calculation unit 26 of consumed electric energy determines that the operation of the reflow soldering apparatus 100 is started, then the operation goes to steps S110, S120 and S130, respectively. If the calculation unit 26 of consumed electric energy determines that the operation of the reflow soldering apparatus 100 is not started, then the operation waits until the operation of the reflow soldering apparatus 100 is started.

At the step S110, the calculation unit 26 of consumed electric energy obtains the amount of operation Dtr from the temperature controllers 20 and calculates consumed electric energy of the heaters 12 from output voltage, output current and the like included in the amount of operation Dtr thus obtained.

This enables an amount of consumed electric energy of the heaters 12 disposed on upper and lower positions of the conveyor 28 of the preliminary heating zone Z1 and the main heating zone Z2.

At the step S120, the calculation unit 26 of consumed electric energy obtains the amount of current Dir from the inverters 22 and calculates amount of consumed electric energy of the inverter 22 from the amount of current Dir thus obtained and the voltage value of the power source unit 32. This enables an amount of consumed electric energy of the fans 14 and the motors 16 disposed on upper and lower positions of the conveyor 28 of the preliminary heating zone Z1 and the main heating zone Z2.

At the step S130, the calculation unit 26 of consumed electric energy obtains the coefficient Dpr of consumed electric energy from the temperature controllers 20, the inverters 22, the control unit 24 and the like and calculates amounts of consumed electric energy of the control unit 24 and the like from the coefficient Dpr of consumed electric energy thus obtained.

At the step S140, the calculation unit 26 of consumed electric energy adds up the amount of consumed electric energy of the heaters 12 calculated at the step S110, the amount of consumed electric energy of the fan 14 calculated at the step S120 and the amount of consumed electric energy of the control unit 24 and the like calculated at the step S130 to calculate the total amount of consumed electric energy of the reflow soldering apparatus 100.

At the step S150, the calculation unit 26 of consumed electric energy controls the operation/display unit 30 to display the total amount of consumed electric energy of the reflow soldering apparatus 100 thus calculated on the representation window 30o in the operation screen of the operation/display unit 30. Such a series of operations for calculating the total amount of the consumed electric energy of the reflow soldering apparatus 100 is performed on a real-time basis or at regular interval. The total amount of the consumed electric energy of the reflow soldering apparatus 100 is then displayed one by one on the operation screen 30a of the operation/display unit 30.

As described above, in the first embodiment, the calculation unit 26 of consumed electric energy calculates amounts of consumed electric energy of the heaters 12 and the motors 16 and the operation/display unit 30 displays the calculated total amount of the consumed electric energy of the reflow soldering apparatus 100 on the representation window 30o of the operation/display unit 30. This enables electricity meters installed in each of the heaters 12 or each of the motors 16 in the past soldering apparatus to be unnecessary so that it is possible to reduce any spaces for installing the electricity meters in the soldering apparatus. Further, an electricity meter installed in each of the parts of the reflow soldering apparatus may be unnecessary so that it is possible to reduce any costs in the reflow soldering apparatus 100.

2. Second Embodiment

Although a case where the invention is applied to the reflow soldering apparatus 100 has been described in the first embodiment, the following will describe a case where the invention is applied to a flow soldering apparatus 200.

[Configuration Example of Flow Soldering Apparatus]

Figure 6:
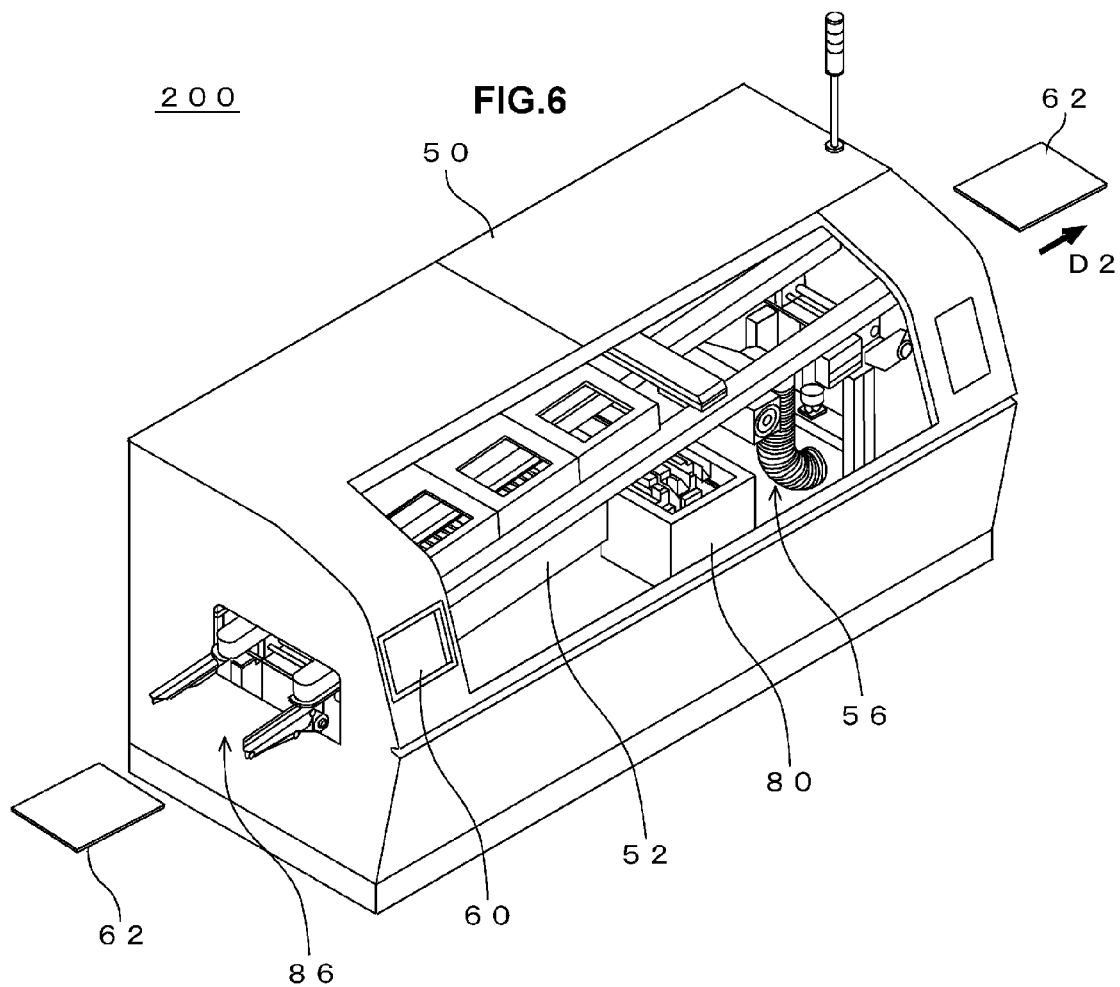
FIG. 6 is a diagram showing a configuration example of a flow soldering apparatus as a second embodiment of the invention.

A configuration of the flow soldering apparatus 200 will be first described. It is to be noted that an opening and shutting door provided on a front of the casing 50 of the main body will be omitted for a brief description thereof and is not shown in FIG. 6. The flow soldering apparatus 200 as the second embodiment of the invention contains the casing 50 of the main body of the flow soldering apparatus 200, a conveyor 86, preheaters 52, a flow solder bath 80, a cooling device 56 and an operation/display unit 60, as shown in FIG. 6. The casing 50 of main body of the flow soldering apparatus 200 is a casing for covering whole of the conveyor 86, the preheaters 52, the flow solder bath 80, the cooling device 56, the operation/display unit 60 and the like and has a function of protecting a printed circuit board 62 so that any particles such as dirt entered from outside cannot be adhered to the printed circuit board 62.

The operation/display unit 60 is composed of, for example, a touch panel operation device and a display device such as liquid crystal display or an organic electroluminescent display so that they are incorporated. The operation/display unit 60 is provided on a front surface of the casing 50 of main body of the flow soldering apparatus 200 and an entrance side thereof. The operation/display unit 60 displays the total amount of consumed electric energy of the flow soldering apparatus 200 based on the information on consumed electric energy supplied from the calculation unit 74 of consumed electric energy on the operation screen of the operation/display unit (see FIG. 8).

The preheaters 52 are used for allowing to dry the printed circuit board 62 to which flux is applied in a fluxing step that is a preceding step of a step where the printed circuit board on which electronic components, not shown, are mounted enters into the flow soldering apparatus 200. The preheaters 52 are also used for heating the printed circuit board 62 to enhance adhesion power in the solder.

The flow solder bath 80 is disposed on a downstream side of the preheaters 52 along a conveying direction D2 of the printed circuit board 62. The flow solder bath 80 contains melted solder for soldering electronic components mounted on the printed circuit board 62 to the printed circuit board 62. As the melted solder, any lead-free solder containing tin-silver-copper or tin-zinc-bismuth may be used. Such solder has a melting range of, for example, about 180° C. through 220° C. The flow solder bath 80 is provided with a primary flow nozzle, not shown, for allowing the solder to flow and generating rough waves and a secondary flow nozzle, not shown, for allowing the solder to flow and generating smooth waves. The primary and secondary flow nozzles blow the melted solder to the printed circuit board 62 heated by the preheaters 52 at a flat level. It is to be noted that the flow solder bath 80 is provided a heater (s), not shown. Temperature of this heater is controlled by a temperature controller 70 so that the heater can melt the solder and holds the solder at a predetermined temperature.

The cooling device 56 is disposed on a downstream side of the flow solder bath 80 along a conveying direction D2 of the printed circuit board 62. The cooling device 56 cools the printed circuit board 62 heated by the preheaters 52 and the flow solder bath 80.

Figure 7:
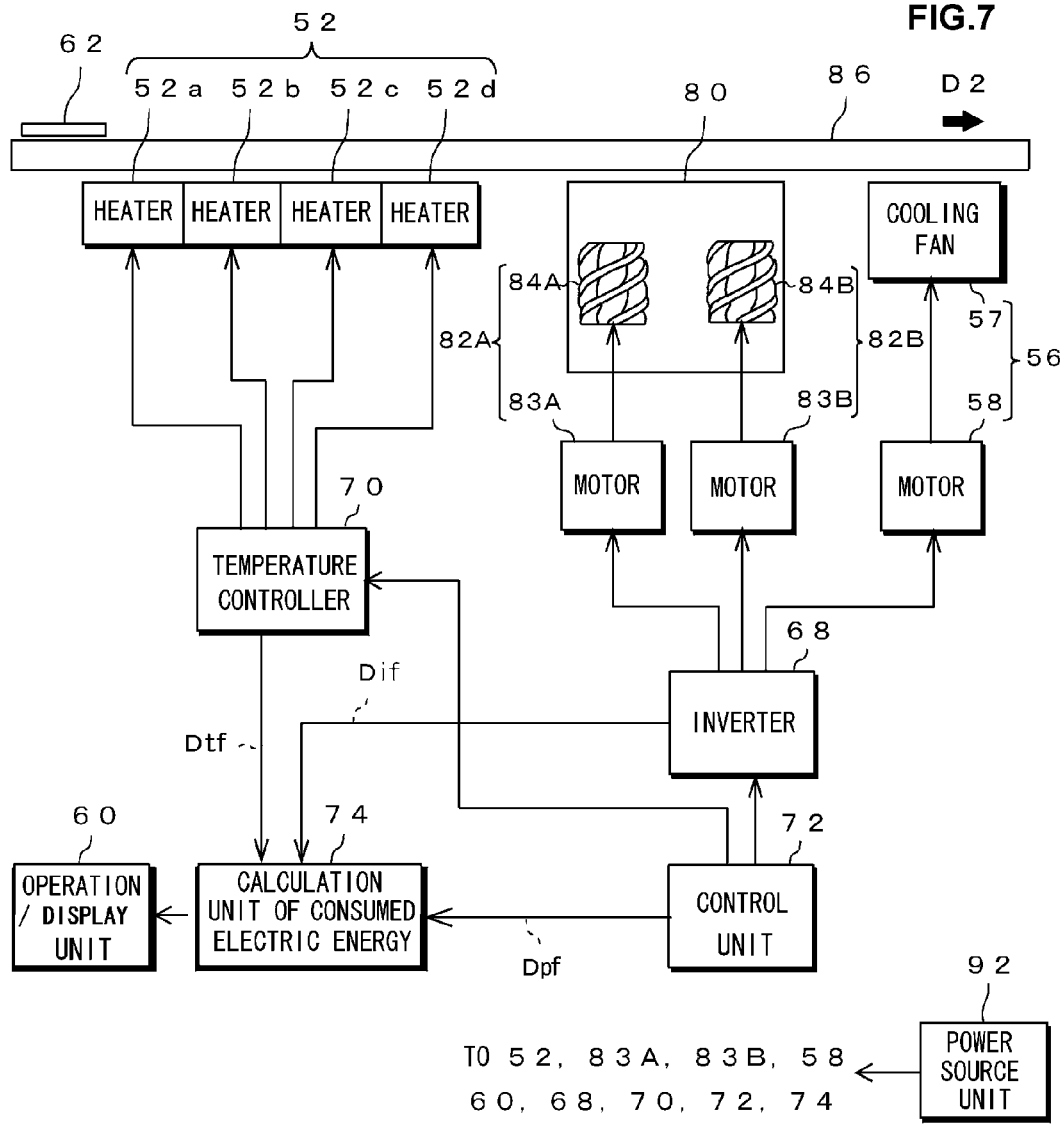
FIG. 7 is a block diagram showing a configuration of the flow soldering apparatus.

The following will describe an internal configuration of the above-mentioned flow soldering apparatus 200 with reference to the block diagram of FIG. 7. As shown in FIG. 7, the flow soldering apparatus 200 contains a power source unit 92, the conveyor 86, the preheaters 52, the temperature controller 70, a first pump 82A for flowing the melted solder from the primary flow nozzle, a second pump 82B for flowing the melted solder from the secondary flow nozzle, the cooling device 56, an inverter 68, a control unit 72, a calculation unit 74 of consumed electric energy and the operation/display unit 60.

The power source unit 92 is connected to the preheaters 52, the temperature controller 70, the first pump 82A, the second pump 82B, the cooling device 56, the inverter 68, the control unit 72, the calculation unit 74 of consumed electric energy and the operation/display unit 60, respectively and supplies power source to each of the parts.

In this embodiment, four preheaters 52a, 52b, 52c and 52d constitute the preheaters 52 and are disposed so that they are adjacent to each other along the conveying direction D2 of the printed circuit board 62. The preheaters 52 heat air within the casing 50 of the main body of the flow soldering apparatus 200 under power control (for example, PID control) of the temperature controller 70.

The temperature controller 70 controls temperature of the four preheaters 52a, 52b, 52c and 52d and has temperature sensors and temperature adjustment units, not shown. The temperature sensors are disposed on respective preheaters 52a, 52b, 52c and 52d to be controlled and measure temperature of each of the preheaters 52a, 52b, 52c and 52d. The temperature adjustment units perform PID control based on temperature information detected by the temperature sensors. In the PID control, the amount of operation Dtf is adjusted so that it becomes a set temperature (target temperature). The amount of operation Dtf includes output voltage, output current or the like of each of the preheaters 52a, 52b, 52c and 52d, on which the temperature of each of the preheaters 52a, 52b, 52c and 52d is set to the set temperature. Further, the temperature controller 70 detects the amount of operation Dtf of the temperature controller 70 when the temperature of the preheaters 52a, 52b, 52c and 52d are controlled and output it to the calculation unit 74 of consumed electric energy.

The first pump 82A supplies the melted solder to the primary flow nozzle, not shown, and contains a motor 83A and a screw 84A. The motor 83A drives under the frequency control by the inverter 68 to rotate the screw 84A at a predetermined number of revolutions. The screw 84A rotates by the driving of the motor 83A to supply the melted solder to the primary flow nozzle.

The second pump 82B supplies the melted solder to the secondary flow nozzle, not shown, and contains a motor 83B and a screw 84B. The motor 83B drives under the frequency control by the inverter 68 to rotate the screw 84B at a predetermined number of revolutions. The screw 84B rotates by the driving of the motor 83B to supply the melted solder to the secondary flow nozzle.

The cooling devices 56 contains a cooling fan 57 and a motor 58 that is connected to the cooling fan 57. The motor 58 drives under a frequency control by the inverters 68 to rotate the cooling fan 57 at a predetermined number of revolutions. The cooling fan 57 is composed of, for example, a sirocco-fan and rotates by the driving of the motor 57 to blow cooled air to the printed circuit board 62.

The inverter 68 in connected to the motors 83A, 83B and 58, respectively, and converts a frequency of power source (alter an amount of current Dir) based on any control information supplied from the control unit 72 to control the number of revolutions of each of the motors 83A, 83B and 58. The inverter 68 also detects and obtains the amount of current Dif output when it controls the motors 83A, 83B and 58 to rotate and outputs the amount of current Dif to the calculation unit 74 of consumed electric energy.

The calculation unit 74 of consumed electric energy is connected to the temperature controller 70, the inverter 68 and the control unit 72, respectively, and is composed of, for example, a sequencer having CPU, ROM, RAM and the like. The calculation unit 74 of consumed electric energy obtains the amount of operation Dtf from the temperature controller 70 and calculates consumed electric energy of the preheaters 52a, 52b, 53c and 53d from the amount of operation Dtf thus obtained. The calculation unit 74 of consumed electric energy also obtains the amount of current Dif used for driving the motors 83A, 83B and 58 from the inverter 68 and calculates consumed electric energy of the motors 83A, 83B and 58 from the amount of current Dif thus obtained. The calculation unit 74 of consumed electric energy further obtains the coefficient Dpf of consumed electric energy from the control unit 72, the inverter 68 and the like and calculates consumed electric energy of the control unit 72 and the like from the coefficient Dpf of consumed electric energy thus obtained.

Next, the calculation unit 74 of consumed electric energy adds up the calculated amount of consumed electric energy of the temperature controller 70, the calculated amount of consumed electric energy of the inverter 68 and the calculated amount of consumed electric energy of the temperature controller 70, and the calculated amount of consumed electric energy of the control unit 72 to calculate a total amount of consumed electric energy of the flow soldering apparatus 200. The calculation unit 74 of consumed electric energy then outputs image information on the calculated total amount of consumed electric energy of the flow soldering apparatus 200 to the operation/display unit 60.

Figure 8:
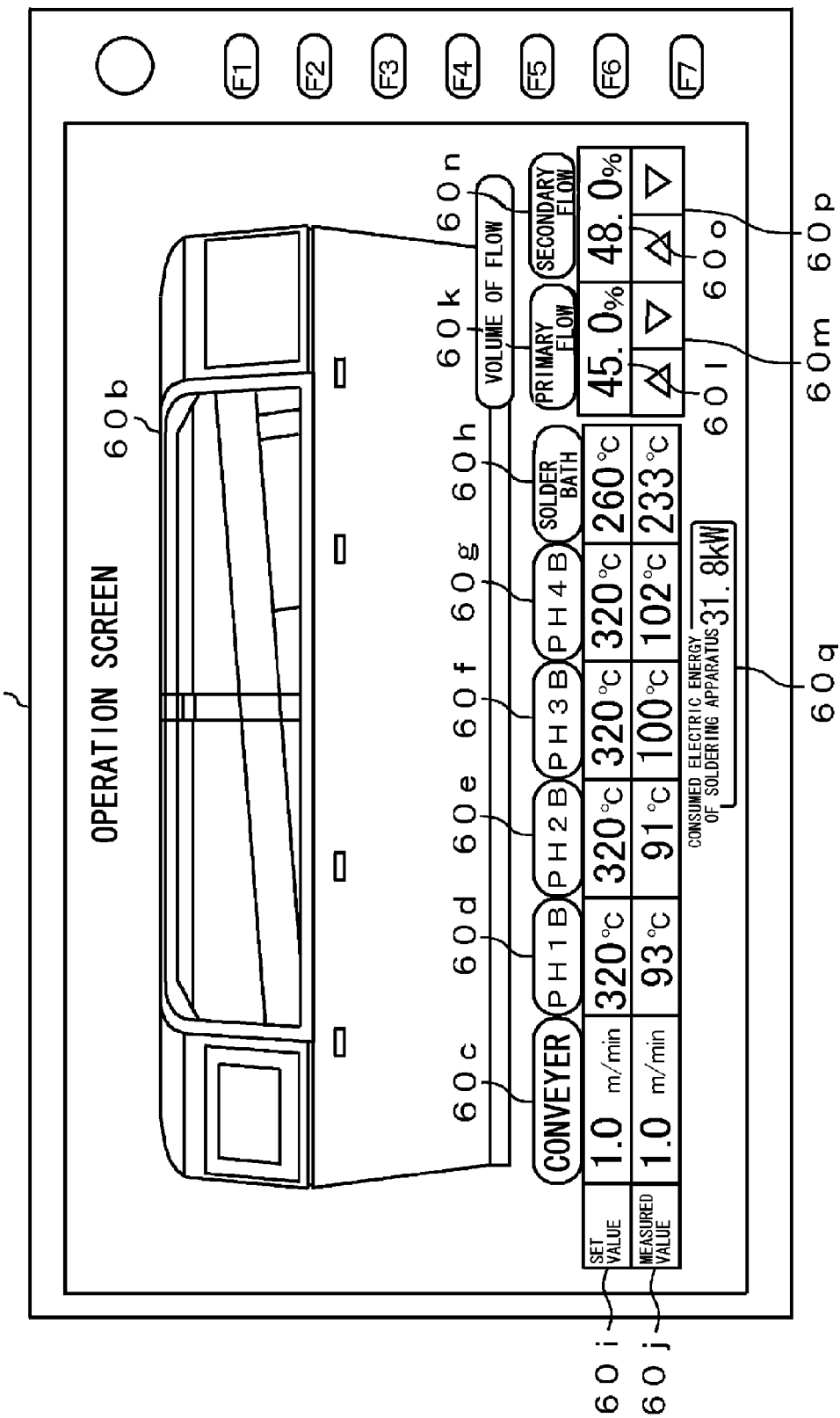
FIG. 8 is a diagram (No. 1) showing a representation example of a screen of an operation/display unit in the flow soldering apparatus.

The operation/display unit 60 displays the total amount of consumed electric energy of the flow soldering apparatus 200 based on the image information on the consumed electric energy supplied from the calculation unit 74 of consumed electric energy on the operation screen of the operation/display unit 60 (see FIG. 8). The operation/display unit 60 also inputs setting of the temperature of each of the preheaters 52 and setting of an amount of flown solder by user's control of the operation screen and supplies the input operation information to the control unit 72.

[Representation Example of Operation Screen in Display Panel of Flow Soldering Apparatus]

The following will describe a representation example of an operation screen 60a to be displayed on the operation/display unit 60. As shown in FIG. 8, the operation screen 60a for setting and performing a speed of the conveyor 86 and temperature of each of the preheaters 52, the conveyor and preheaters constituting the flow soldering apparatus, and for displaying actual temperatures of the preheaters 52 and actual speed of the conveyor 86 at the current operation time thereof, appears in the operation/display unit 60.

An image 60b of the flow soldering apparatus 200, which indicates the flow soldering apparatus 200 schematically, appears at a middle of the operation screen 60a of the operation/display unit 60. Below the image 60b of the flow soldering apparatus and at the left side of the operation screen 60a, a conveyor-speed setting button 60c for setting a conveying speed of the conveyor 86 is shown. If the button 86 is pressed, a numerical key, not shown, appears on the operation screen 60a. By inputting a desired numerical value using the numerical key, it is possible to set the conveying speed of the conveyor 86 optionally.

At right side of the conveyor-speed setting button 60c, preheater-temperature-setting buttons 60d, 60e, 60f and 60g for setting temperature of each of the preheaters 52a, 52b, 52c and 52d (see FIG. 7) are shown so that the buttons are arranged on the operation screen 60a from left to right in order. At right side of the preheater-temperature-setting button 60g, a solder-bath-temperature-setting button 60h for setting temperature of melted solder in the solder bath 80 is shown.

Below the conveyor-speed setting button 60c, the preheater-temperature-setting buttons 60d, 60e, 60f and 60g and solder-bath-temperature-setting button 60h, respectively, their set temperature display windows 60i are shown. On the set temperature display windows 60i, these set temperatures which a user sets using the buttons are shown.

Below the set temperature display windows 60i, measured temperature display windows 60j are shown. On these measured temperature display windows 60j, an actual measured speed of the conveyor 86, actual measured temperatures of the preheaters 52, and actual measured temperature of the melted solder in the solder bath 54 are shown.

At right side of the solder-bath-temperature-setting button 60h, a primary-flow-nozzle-setting button 60k for switching on/off the flow of the melted solder flown from the primary nozzle is shown. If the primary-flow-nozzle-setting button 60k is pressed, for example, the flow of the melted solder is switched on so that the melted solder starts flowing from the primary nozzle. Below the primary-flow-nozzle-setting button 60k, a measured amount-of-flown-solder display window 60l for displaying an actual amount of solder flown from the primary nozzle is shown. Below the measured amount-of-flown-solder display window 60l, a pair of up-down arrow keys 60m for adjusting an amount of melted solder flown from the primary nozzle is shown. It is possible to set a numerical value of the amount of melted solder flown from the primary nozzle by using the up-down arrow keys 60m. The amount of melted solder may be adjusted by controlling, for example, a number of revolutions of the motor 83A.

At right side of the primary-flow-nozzle-setting button 60k, a secondary-flow-nozzle-setting button 60n for switching on/off the flow of the melted solder flown from the secondary nozzle is shown. If the secondary-flow-nozzle-setting button 60n is pressed, for example, the flow of the melted solder is switched on so that the melted solder starts flowing from the secondary nozzle. Below the secondary-flow-nozzle-setting button 60n, a measured amount-of-flown-solder display window 60o for displaying an actual amount of solder flown from the secondary nozzle is shown. Below the measured amount-of-flown-solder display window 60o, a pair of up-down arrow keys 60p for adjusting an amount of melted solder flown from the secondary nozzle is shown. It is possible to set a numerical value of the amount of melted solder flown from the secondary nozzle by using the up-down arrow keys 60p. The amount of melted solder may be adjusted by controlling, for example, a number of revolutions of the motor 83B.

An indication window 60q for indicating the total amount of consumed electric energy of whole of the flow soldering apparatus 200 is shown at middle of the operation screen 60a and below the preheater-temperature-setting buttons 60d, 60e, 60f and 60g. In the indication window 60q, the total amount of the consumed electric energy of flow soldering apparatus 200, which have been calculated in the above-mentioned calculation unit 74 of consumed electric energy, is displayed on a real-time basis or at regular interval.

Figure 9:
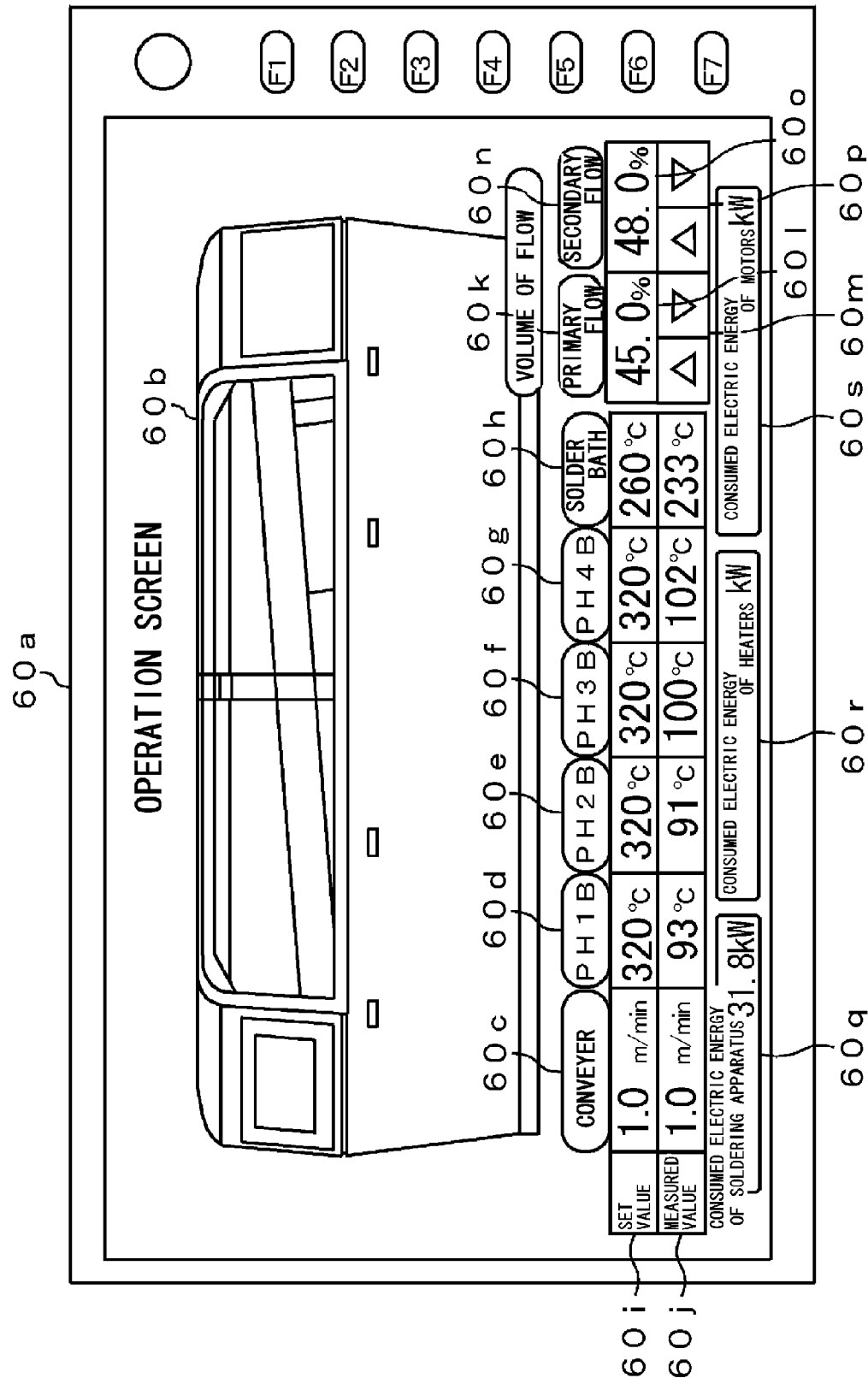
FIG. 9 is a diagram (No. 2) showing the representation example of the screen of the operation/display unit in the flow soldering apparatus.

It is to be noted that an indication window for indicating consumed electric energy of respective parts such as the preheaters 52 or the motors 83A, 83B and 68 other than the indication window 60q indicating the total amount of consumed electric energy of flow soldering apparatus 200 may be shown. For example, as shown in FIG. 9, a preheater-consumed-electric-energy-indicating window 60r for indicating consumed electric energy of the preheaters 52 may be shown at a right side of the indication window 60q. A motor-consumed-electric-energy-indicating window 60s for indicating consumed electric energy of the motors 83A, 83B and 68 may be shown at a right side of the preheater-consumed-electric-energy-indicating window 60r. This enables the consumed electric energy of the parts of the flow soldering apparatus 200 to be known in detail so that the consumed electric energy of the flow soldering apparatus 200 can be controlled in detail. As a result thereof, efficient energy saving of whole of the flow soldering apparatus 200 can be accomplished.

[Operation Example of Flow Soldering Apparatus]

The following will describe an operation example of the flow soldering apparatus 200 according to the invention. As shown in FIG. 10, at step S200, the calculation unit 74 of consumed electric energy determines whether or not the operation of the flow soldering apparatus 200 is started. For example, it determines whether or not the user selects an operation button for powering the power source on in the operation/display unit 60. If the calculation unit 74 of consumed electric energy determines that the operation of the flow soldering apparatus 200 is started, then the operation goes to steps S210, S220 and S230, respectively. If the calculation unit 74 of consumed electric energy determines that the operation of the flow soldering apparatus 200 is not started, then the operation waits until the operation of the flow soldering apparatus 200 is started.

At the step S210, the calculation unit 74 of consumed electric energy obtains the amount of operation Dtf from the temperature controller 70 and calculates consumed electric energy of the preheaters 52 from output voltage, output current and the like included in the amount of operation Dtf thus obtained.

At the step S220, the calculation unit 74 of consumed electric energy obtains the amount of current Dif from the inverter 68 and calculates amount of consumed electric energy of the motors 83A, 83B and 58 from the amount of current Dif thus obtained and the voltage value supplied from the power source unit 92.

At the step S230, the calculation unit 74 of consumed electric energy obtains the coefficient Dpf of consumed electric energy from the temperature controller 70, the inverter 68, the control unit 72 and the like and calculates amounts of consumed electric energy of the control unit 72 and the like from the coefficient Dpf of consumed electric energy thus obtained.

At the step S240, the calculation unit 74 of consumed electric energy adds up the amount of consumed electric energy of the preheaters 52 calculated at the step S210, the amount of consumed electric energy of the motors 83A, 83B and 58 calculated at the step S220 and the amount of consumed electric energy of the control unit 72 and the like calculated at the step S230 to calculate the total amount of consumed electric energy of the flow soldering apparatus 200.

At the step S250, the calculation unit 74 of consumed electric energy controls the operation/display unit 60 to display the total amount of consumed electric energy of the flow soldering apparatus 200 thus calculated on the indication window 60q in the operation screen 60a of the operation/display unit 60. Such a series of operations for calculating the total amount of the consumed electric energy of the flow soldering apparatus 200 is performed on a real-time basis or at regular interval. The total amount of the consumed electric energy of the flow soldering apparatus 200 is then displayed one by one on the operation screen 60a of the operation/display unit 60. It is to be noted that when the total amount of the consumed electric energy of flow soldering apparatus 200 exceeds a predetermined value, the indication window 60q may be flushed or highlighted.

As described above, in the second embodiment, the calculation unit 74 of consumed electric energy calculates amounts of consumed electric energy of the preheaters 52 and the motors 83A, 83B and 58 and the operation/display unit 60 displays the calculated total amount of the consumed electric energy of the flow soldering apparatus 200 on the indication window 60q of the operation/display unit 60. This enables electricity meters installed in each of the preheaters 52 or each of the motors 83A, 83B and 58 in the past soldering apparatus to be unnecessary so that it is possible to reduce any spaces for installing the electricity meter in the flow soldering apparatus 200. Further, an electricity meter installed in each of the parts of the flow soldering apparatus 200 may be unnecessary so that it is possible to reduce any costs in the flow soldering apparatus 200.

The invention is not limited to the above-mentioned embodiments and it should be understood by those skilled in the art that various modifications, combinations, sub-combinations and alterations may occur depending on design requirements and other factors insofar as they are within the scope of the appended claims or the equivalents thereof. Although it has been described in the above-mentioned embodiments that the control unit 24 or 72 and the calculation unit 26 or 74 of consumed electric energy are separately composed, the invention is not limited thereto. The control unit 24 or 72 and the calculation unit 26 or 74 of consumed electric energy are composed as one body.

What is claimed is:

1. A soldering apparatus that solders an electronic component on a circuit board using a solder composition, the apparatus comprising:
   a soldering unit that solders the electronic component on the circuit board;
   a detection unit that detects information of consumed electric energy relating to an amount of the consumed electric energy of the soldering unit and information of consumed electric energy of the detection unit;
   a calculation unit that calculates a total amount of the consumed electric energy of the soldering apparatus;
   a control unit that controls the detection unit and the calculation unit and sends a previously set coefficient of consumed electric energy of the control unit as information on its consumed electric energy to the calculation unit; and
   a display unit that displays on a screen thereof the total amount of the consumed electric energy of the soldering apparatus, which is calculated by the calculation unit, wherein the calculation unit obtains the information of consumed electric energy of the soldering unit, the information of consumed electric energy of the detection unit, and the information of consumed electric energy of the control unit, and calculates the total amount of the consumed electric energy of the soldering apparatus based on the obtained information of consumed electric energy of the soldering unit, the obtained information of consumed electric energy of the detection unit, and the obtained information of consumed electric energy of the control unit.

2. The soldering apparatus according to claim 1, wherein the soldering apparatus contains a reflow soldering apparatus that solders the electronic component on the circuit board to which the solder composition is previously applied,
   the soldering unit contains a heater that heats air within the reflow soldering apparatus, and
   the detection unit contains a temperature controller that controls temperature of the heater and outputs an amount of operation of the temperature controller to the calculation unit as the information of consumed electric energy of the detection unit.

3. The soldering apparatus according to claim 1, wherein the soldering apparatus contains a reflow soldering apparatus that solders the electronic component on the circuit board to which the solder composition is previously applied,
   the soldering unit contains a motor which drives a fan that blows air heated within the reflow soldering apparatus to the solder composition, and
   the detection unit contains an inverter that controls a revolution of the motor and outputs an amount of current in the inverter to the calculation unit as the information of consumed electric energy of the detection unit.

4. The soldering apparatus according to claim 1, wherein the soldering apparatus contains a flow soldering apparatus that solders the electronic component, which is previously mounted on the circuit board, on the circuit board by using flowed solder,
   the soldering unit contains a heater that preliminarily heats the circuit board, and
   the detection unit contains a temperature controller that controls temperature of the heater and outputs an amount of operation of the temperature controller to the calculation unit as the information of consumed electric energy of the detection unit.

5. The soldering apparatus according to claim 1, wherein the soldering apparatus contains a flow soldering apparatus that solders the electronic component, which is previously mounted on the circuit board, on the circuit board by using flowed solder,
   the soldering unit contains a motor that drives a fan that blows air to a joint portion of the electronic component and the circuit board to which the solder composition is flowed and cools the solder composition, and
   the detection unit contains an inverter that controls a revolution of the motor and outputs an amount of current to the calculation unit as the information of consumed electric energy of the detection unit.

6. The soldering apparatus according to claim 1, wherein the soldering unit comprises a heater for heating air and a motor that drives a fan to blow air heated by the heater for heating the solder composition, the detection unit comprises a temperature sensor that measures temperature near the heater and a temperature adjustment unit that controls the heater based on the temperature measured by the temperature sensor and adjusts an amount of operation so that the measured temperature becomes a target temperature, and the detection unit outputs the amount of operation to the calculation unit as information of consumed electric energy of the heater.

7. The soldering apparatus according to claim 6, wherein the detection unit comprises an inverter that supplies current to the motor for driving the fan and a control unit that supplies control information to the inverter for controlling speed of the motor, and the inverter detects an amount of the current supplied to the motor and outputs the amount of current to the calculation unit as information of consumed electric energy of the motor.

8. A method of operating a soldering apparatus that solders an electronic component on a circuit board using a solder composition, the apparatus comprising a soldering unit that solders the electronic component on the circuit board, a detection unit that detects information of consumed electric energy relating to an amount of the consumed electric energy of the soldering unit and information of consumed electric energy of the detection unit, a calculation unit that calculates a total amount of the of consumed electric energy of the soldering apparatus, and a control unit that controls the detection unit and the calculation unit and sends a previously set coefficient of consumed electric energy of the control unit as information on its consumed electric energy to the calculation unit; the method comprising:
   receiving the information of consumed electric energy of the soldering unit, the information of consumed electric energy of the detection unit, and the information of consumed electric energy of the control unit, and calculating a total amount of the consumed electric energy of the soldering apparatus based on the received information of consumed electric energy of the soldering unit, the received information of consumed electric energy of the detection unit, and the obtained information of consumed electric energy of the control unit; and
   displaying the calculated total amount of the consumed electric energy of the soldering apparatus on a screen of a display unit.

9. The method according to claim 8, wherein the soldering unit comprises a heater for heating air and a motor that drives a fan to blow air heated by the heater for heating solder, and the method comprises employing the detection unit to measure temperature near the heater and to control the heater by adjusting an amount of operation so that the measured temperature becomes a target temperature, and outputting the amount of operation as information of consumed electric energy of the heater.

10. The method according to claim 9, wherein the detection unit comprises an inverter that supplies current to the motor for driving the fan and a control unit that supplies control information to the inverter for controlling speed of the motor, and the method comprises employing the inverter to detect an amount of the current supplied to the motor and output the amount of current to the calculation unit as information of consumed electric energy of the motor.

* * * * *